(12) United States Patent
Chen et al.

(10) Patent No.: US 11,618,729 B2
(45) Date of Patent: Apr. 4, 2023

(54) METHOD OF PREPARING BILIRUBIN-IX α FROM BILIVERDIN-IX α DIESTER

(71) Applicants: Poseidon Pharmaceutical Co., Ltd., Hong Kong (CN); Wuhan Dapeng Pharmaceutical Co., Ltd., Wuhan (CN)

(72) Inventors: Fapu Chen, Wuhan (CN); Yuxin Shi, Wuhan (CN); Fakai Chen, Wuhan (CN)

(73) Assignees: POSEIDON PHARMACEUTICAL CO., LTD., Hong Kong (CN); WUHAN DAPENG PHARMACEUTICAL CO.. LTD., Wuhan (CN)

( * ) Notice: Subject to any disclaimer, the term of this patent is extended or adjusted under 35 U.S.C. 154(b) by 3 days.

(21) Appl. No.: 17/314,035

(22) Filed: May 6, 2021

(65) Prior Publication Data
US 2021/0261506 A1    Aug. 26, 2021

Related U.S. Application Data

(63) Continuation-in-part of application No. PCT/CN2019/088905, filed on May 28, 2019.

(30) Foreign Application Priority Data

Nov. 7, 2018  (CN) .......................... 201811318011.9

(51) Int. Cl.
C07D 207/44    (2006.01)

(52) U.S. Cl.
CPC .................................. *C07D 207/44* (2013.01)

(58) Field of Classification Search
CPC .................................................... C07D 207/44
See application file for complete search history.

(56) References Cited

U.S. PATENT DOCUMENTS 9,242,932 B2 *    1/2016   Takemoto ............ C07D 207/44

* cited by examiner

*Primary Examiner* — Kamal A Saeed
(74) *Attorney, Agent, or Firm* — Matthias Scholl P.C.; Matthias Scholl

(57) ABSTRACT

A method of preparing bilirubin IXα from biliverdin IXα diester, the method including: 1) adding sodium hydroxide dissolved in a first methanol solution to biliverdin IXα diester dissolved in a second methanol solution, to yield a first mixture; adding water to the first mixture to hydrolyze biliverdin IXα diester; adding an acid to the first mixture to adjust the pH value thereof; removing a first solvent of the first mixture through rotary evaporation, and removing an inorganic salt through rinsing, and vacuum drying, to yield biliverdin IXα; and 2) dissolving the biliverdin IXα in an alcoholic solution, and adding a radical scavenger and borohydride to the alcoholic solution, to yield a second mixture; adding a ketone to the second mixture to decompose excess borohydride; adding the acid to the second mixture to adjust the pH value thereof; and removing a second solvent of the second mixture through rotary evaporation.

12 Claims, 6 Drawing Sheets

METHOD OF PREPARING BILIRUBIN-IX α FROM BILIVERDIN-IX α DIESTER

CROSS-REFERENCE TO RELATED APPLICATIONS

This application is a continuation-in-part of International Patent Application No. PCT/CN2019/088905 with an international filing date of May 28, 2019, designating the United States, now pending, and further claims foreign priority benefits to Chinese Patent Application No. 201811318011.9 filed on Nov. 7, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to a method of preparing bilirubin IXα from biliverdin IXα diester.

Bilirubins are a family of bile pigments. They include Bilirubin IXα (compound 1) which has the following formula:

CAS: 635-65-4, molecular formula: $C_{33}H_{36}N_4O_6$, molecular weight: 584.67.

Bilirubin IXα has a wide range of physiological activities and antioxidant function. It can inhibit the oxidation of linoleic acid and phospholipids.

Bilirubin IXα is an orange crystalline solid (powder), but a pure product thereof is difficult to reach a purity of more than 96 wt. %.

Conventionally, biliverdin IXα dimethyl ester (compound 2 in FIG. 1) is hydrolyzed to yield biliverdin IXα (compound 3 in FIG. 1), and then reduced to bilirubin IXα. The reducing agent is tetravalent or low valent sulfur (such as sodium sulfite) or zinc powder-acetic acid system, and the yield is less than 25%.

At present, bilirubin IXα on the market is extracted from the bile of animals (mainly cattle and pigs) with chloroform, and contains a lot of unknown impurities, including a small amount of high molecular impurities (TLC found the impurities were at the origin, and no peak found through HPLC). In addition, the purity of the extracted bilirubin IXα is difficult to reach 97% or more.

SUMMARY

The disclosure provides a method of preparing bilirubin IXα from biliverdin IXα diester, the method comprising:

1) adding sodium hydroxide dissolved in a first methanol solution to biliverdin IXα diester dissolved in a second methanol solution at 5-30° C., to yield a first mixture; adding water to the first mixture to hydrolyze biliverdin IXα diester at 5-30° C.; adding an acid to the first mixture to adjust a pH value thereof to between 4 and 5; removing a first solvent of the first mixture through rotary evaporation, and removing an inorganic salt through rinsing, and vacuum drying, to yield biliverdin IXα; and 2) dissolving the biliverdin IXα in an alcoholic solution, and adding a radical scavenger (stabilizer) and borohydride to the alcoholic solution, to yield a second mixture where the biliverdin IXα is reduced; adding a ketone to the second mixture to decompose excess borohydride; adding the acid to the second mixture to adjust a pH value thereof to between 4 and 5; removing a second solvent of the second mixture through rotary evaporation, and rinsing, and refining with methanol-chloroform to yield bilirubin IXα having a purity of 97%.

In a class of this embodiment, in 1), the biliverdin IXα diester is hydrolyzed at 10-15° C.

In a class of this embodiment, in 2), the radical scavenger includes but comprises an alkylphenol.

In a class of this embodiment, the alkylphenol is tert butyl hydroquinone.

In a class of this embodiment, in 2), the radical scavenger accounts for 0.05-0.5 wt. % of the biliverdin IXα.

In a class of this embodiment, the radical scavenger accounts for 0.1-0.2 wt. % of the biliverdin IXα.

In a class of this embodiment, in 2), the borohydride is selected from the group consisting of zinc borohydride, lithium borohydride, sodium borohydride, and potassium borohydride.

In a class of this embodiment, the borohydride is zinc borohydride.

In a class of this embodiment, in 2), the ketone includes but comprises acetone.

In a class of this embodiment, in 2), the reduction of the biliverdin IXα is monitored by thin layer chromatography (TLC); when the biliverdin IXα is reduced completely, the ketone is added to the second mixture to decompose excess borohydride.

In a class of this embodiment, the acid includes but comprises acetic acid.

In a class of this embodiment, the concentration of acetic acid is 10%.

The following advantages are associated with the method of the disclosure:

In the reduction reaction of the method, the radical scavenger (stabilizer) is added and zinc borohydride is used as a neutral mild reducing agent. Once the reduction reaction is completed, the excess reducing agent is decomposed with ketone immediately, which greatly reduces the side reaction of bilirubin IXα in the reduction reaction and post-treatment process, thus reducing the generation of impurities which are difficult to separate, so the method does not involve in the chromatographic separation, and has high yield (up to 85%) and high purity (more than 97% in HPLC external standard method). The reaction conditions are mild, cost-effective and easy to operate.

DETAILED DESCRIPTION

To further illustrate the disclosure, embodiments detailing a method of preparing bilirubin IXα from biliverdin IXα diester are described below. It should be noted that the following embodiments are intended to describe and not to limit the disclosure.

Conventional reagent: AR grade, national medicine reagent. Thin-Layer Chromatography board: Qingdao Ocean Chemical Plant.

NMR instrument: Bruck 400 MB, Shanghai Institute of Organic Chemistry. HPLC instrument: Agilent 1200.

Biliverdin IXα dimethyl ester of the disclosure is prepared according to the preparation method of Smith, Tetrahedron, Vol. 40, No. 10, page 1749, 1984.

Example 1

Preparation of Biliverdin IXα (Compound 3)

Figure 1:
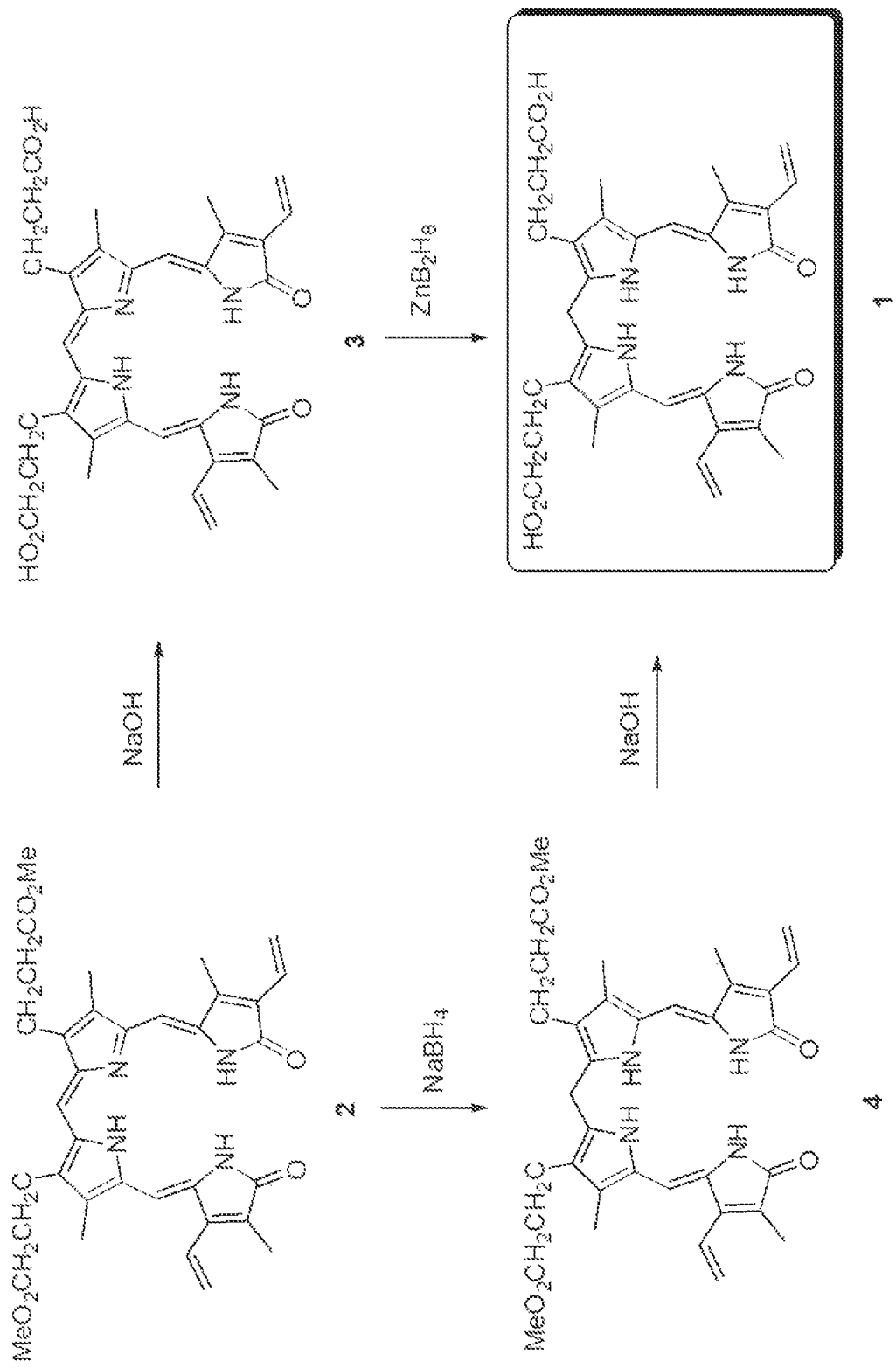
FIG. 1 is a synthetic route of bilirubin IXα in the related art.
Figure 2:
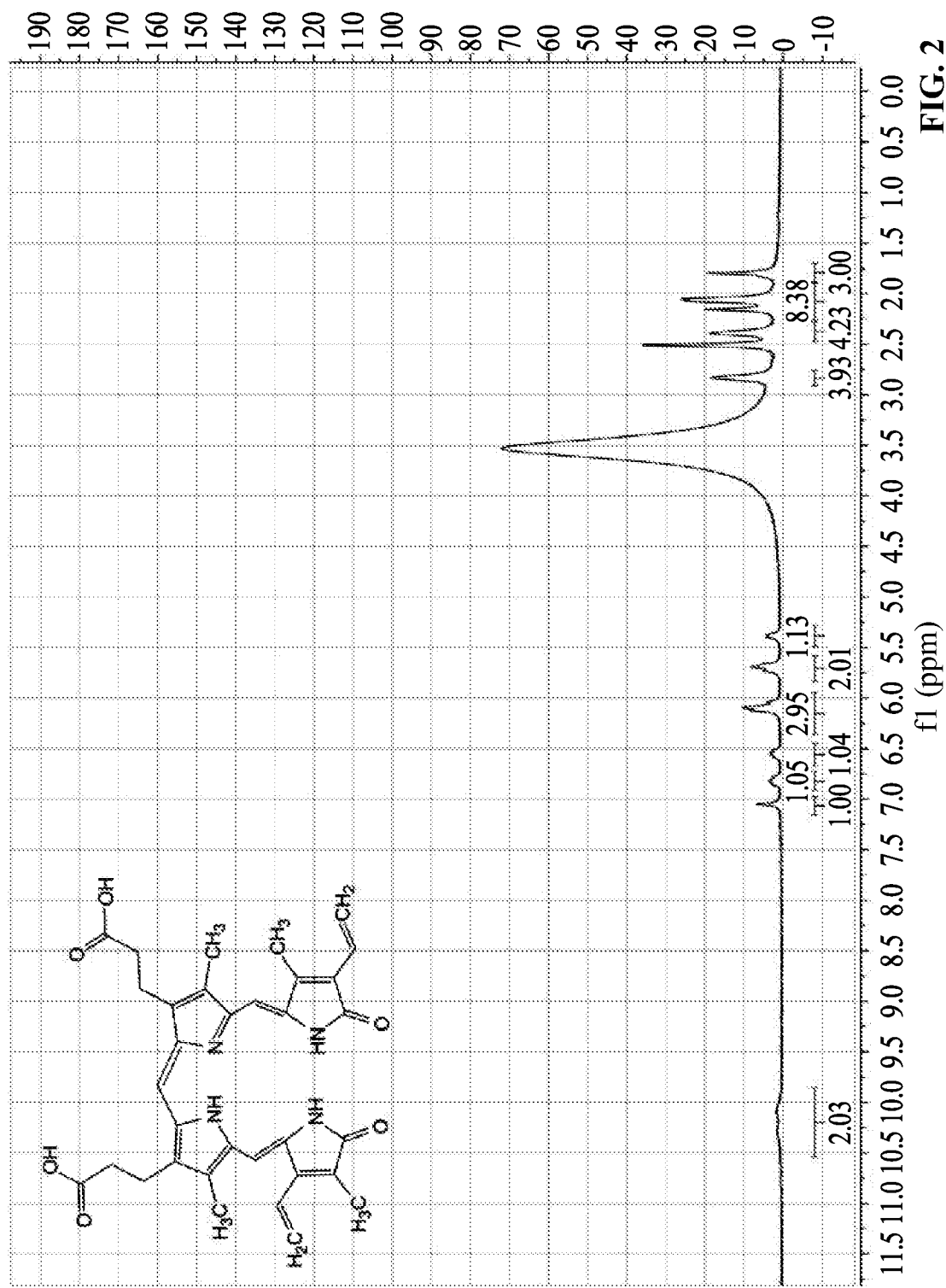
FIG. 2 is a nuclear magnetic resonance (NMR) spectrogram of biliverdin IXα in Example 2.

A): 0.350 g (0.5735 mmol) of biliverdin IXα dimethyl ester and 100 mL of methanol were added to a 250-mL three-mouthed bottle. The mixture was magnetically stirred at room temperature until biliverdin IXα was dissolved completely. Thereafter, a methanol solution (1.38 g, 1.725 mmol) comprising 5% sodium hydroxide was added to the three-mouthed bottle at 10° C., and stirred with the addition of 5 g of water. The mixture was stirred overnight (15 hours) at 10° C. under nitrogen protection. Next day, thin-layer chromatography (developing agent: dichloromethane:ethyl acetate, v/v=50:1) was performed, and the result showed dimethyl ester was hydrolyzed completely. The pH of the mixture was adjusted to 4-5 with 10% acetic acid, and then the solvent was removed through rotary evaporation, thus yielding a green solid. The green solid was mixed with 20 mL of water, stirred for an hour, filtered, and rinsed with 20 mL of water comprising 10 wt. % methanol until the pH was 6. The mixture of the green solid and water was dried overnight in a vacuum over phosphorus pentoxide at room temperature, thereby yielding 0.331 g of blue-green powders, with a yield of 99.1%. $^1$H NMR (DMSO-d6), as shown in FIG. 2.

B): The operations were basically the same as that in A) except that the mixture was stirred overnight at 30° C. under nitrogen protection. 8 hours later, under TLC, the raw material point was disappeared. TLC was performed for the reaction mixture (after neutralization), and tailing phenomenon was observed, which indicated that the increase of the temperature led to the formation of impurities. Following the operations in method A), 0.331 g of blue-green powders were obtained, and then was refined with 50 mL of methanol chloroform (methanol:chloroform, v/v=2:1), to yield 0.305 g of blue-green powders, with the yield of 91.3%. At the temperature of 30° C., although the hydrolysis time was shortened, the side reaction occurred, and the TLC single pure product (point) can be obtained only through refining.

Example 2

Figure 3:
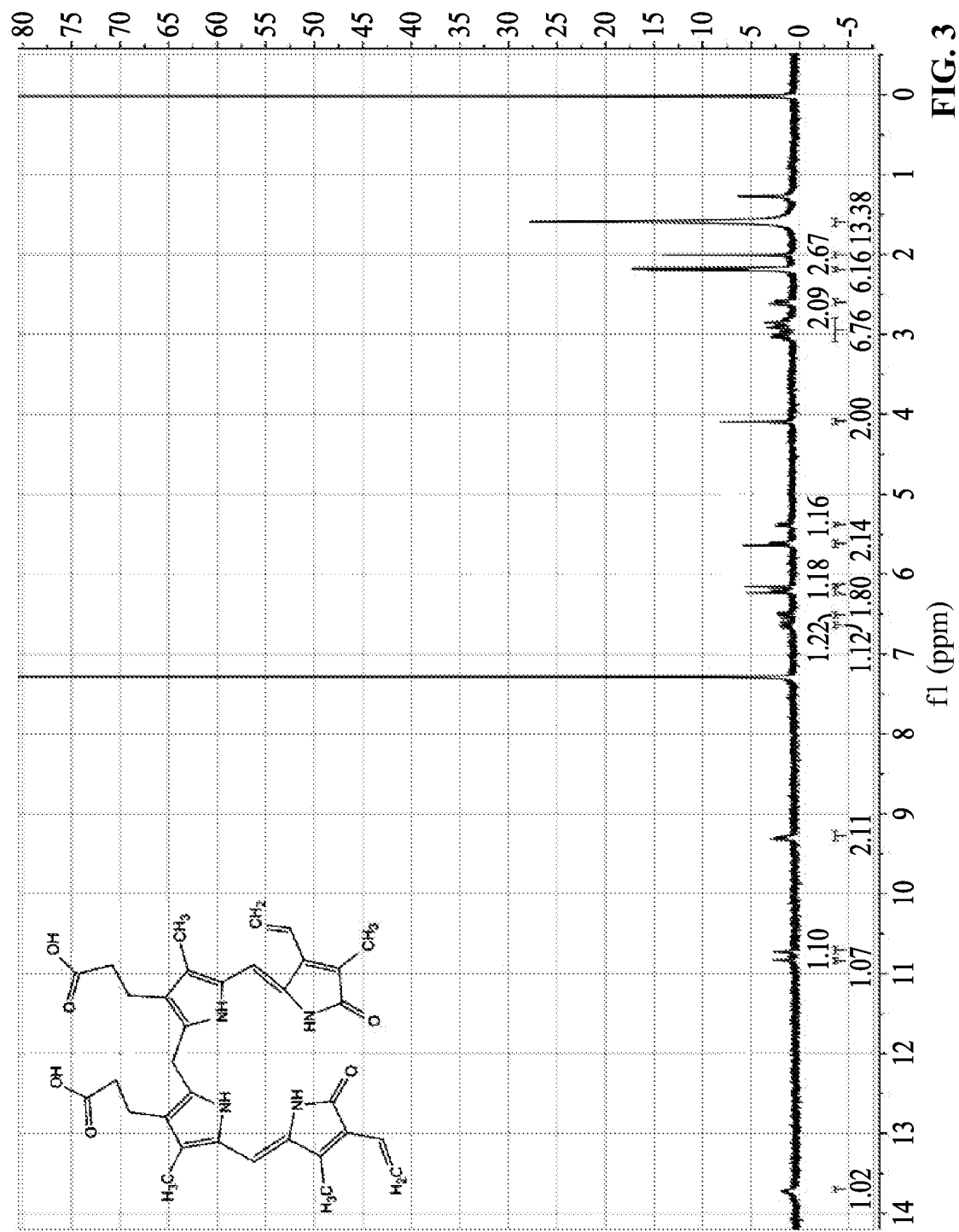
FIG. 3 is a $^1$H NMR (CDCl$_3$) spectrogram of bilirubin IXα in Example 2.
Figure 4:
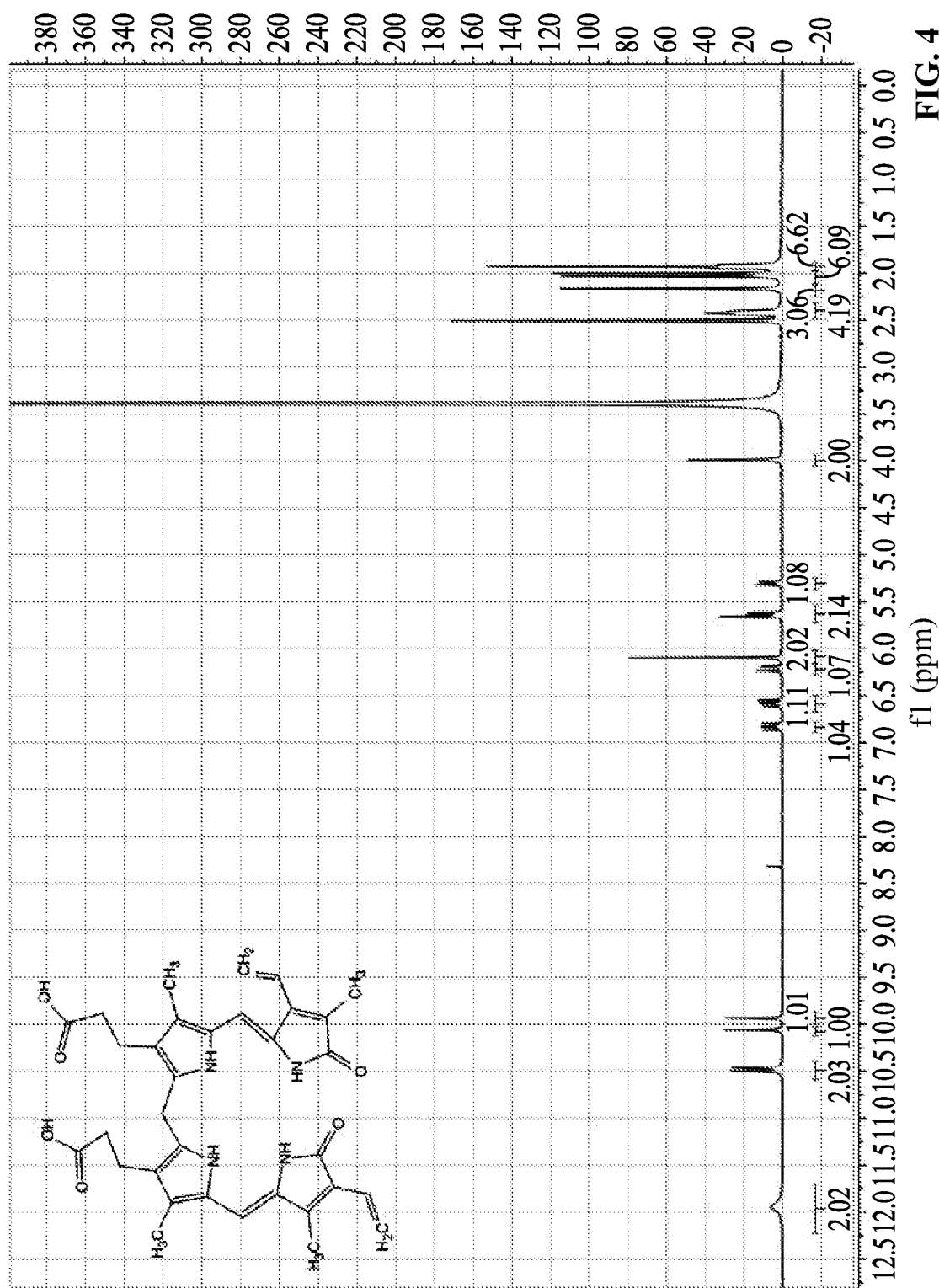
FIG. 4 is a $^1$H NMR (DMSO-d6) spectrogram of bilirubin IXα in Example 2.
Figure 5:
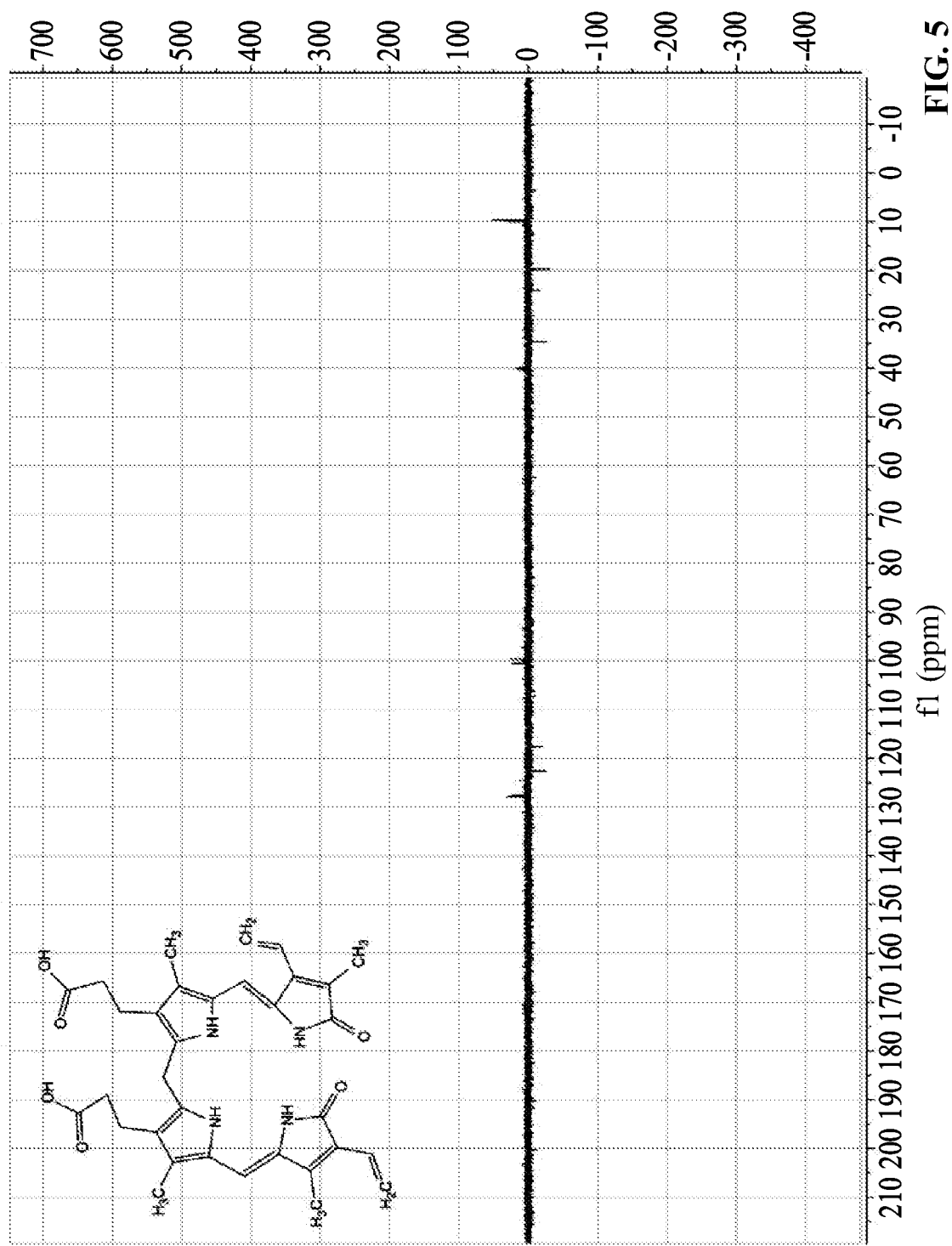
FIG. 5 is a DEPT $^{13}$C NMR (DMSO-d6) spectrogram of bilirubin IXα in Example 2.

Preparation of Bilirubin IXα (Compound 1)
A) Using Zinc Borohydride as Reducing Agent
0.300 g (0.515 mmol) of biliverdin IXα and 300 mL of methanol were added to a 500-mL three-mouthed bottle. The mixture was magnetically stirred at room temperature until biliverdin IXα was dissolved completely. Thereafter, a methanol solution (1 mL) comprising 0.45 mg of tert-butylhydroquinone was added to the three-mouthed bottle at 0° C., and followed by addition of 20 mL of fresh tetrahydrofuran solution comprising 0.245 g of zinc borohydride (2.58 mmol) within 30 min. The color of the reaction solution changed from dark green to light green. The reaction solution was stirred for 10 min, and the color of the reaction solution become light yellow-green. TLC (Methanol:Chloroform v/v=1:50) indicated the presence of yellow and red spots, and the raw material point (green) disappeared. 10 mL of acetone was added to the reaction solution immediately, and gas produced. The mixture was stirred for 15 minutes until no gas was produced. The pH of the reaction solution was adjusted to 4-5 using 10% acetic acid. The reaction solution was stirred for 10 min, and then the solvent was removed through rotary evaporation, thus yielding a red-orange solid. The red-orange solid was mixed with 20 mL of water, stirred for an hour, filtered, and rinsed with 20 mL of water comprising 10 wt. % methanol until the pH was 6. Red-orange powders were obtained. The powders were mixed with 30 mL of 2:1 (v/v) methanol-chloroform and stirred at room temperature for 2 hours, then cooled to 10° C., filtered, rinsed with 6 mL of 2:1 (v/v) methanol-chloroform, and dried overnight at room temperature in the phosphorus pentoxide vacuum conditions, thereby yielding 0.259 g of red-orange powders, with a yield of 86.0%. $^1$H NMR (CDCl$_3$) as shown in FIG. 3, $^1$H NMR (DMSO-d6) as shown in FIG. 4, DEPT $^{13}$C NMR (DMSO-d6) as shown in FIG. 5.

Content determination: Chromatographic conditions and system applicability test: octadecylsilane bonded silica gel was used as filler; the detection wavelength was 450 nm. The number of theoretical plates should not be less than 3000 according to bilirubin peak.

Preparation of control solution: an appropriate amount of bilirubin reference (dried to constant weight, stored at low temperature) was weighed and dichloromethane was added to yield a solution containing 12 μg of bilirubin reference per 1 mL of the solution.

Preparation of test solution: about 10 mg of a test product was weighed and added to a 50-mL volumetric flask, and appropriate amount of dichloromethane was added to be level with the graduation mark, and shaken evenly. 3 mL of the solution was collected, added to a 50-mL volumetric flask, and dichloromethane was added to dilute the solution to be level with the graduation mark. The mixed solution was shaken evenly, filtered with a 0.45-μm microporous membrane, and then the filtrate was taken.

Determination method: 5 μL of the control solution and 5 μL of the test solution were precisely sampled and injected into the liquid chromatograph for determination. The content was calculated by external standard method.

Figure 6:
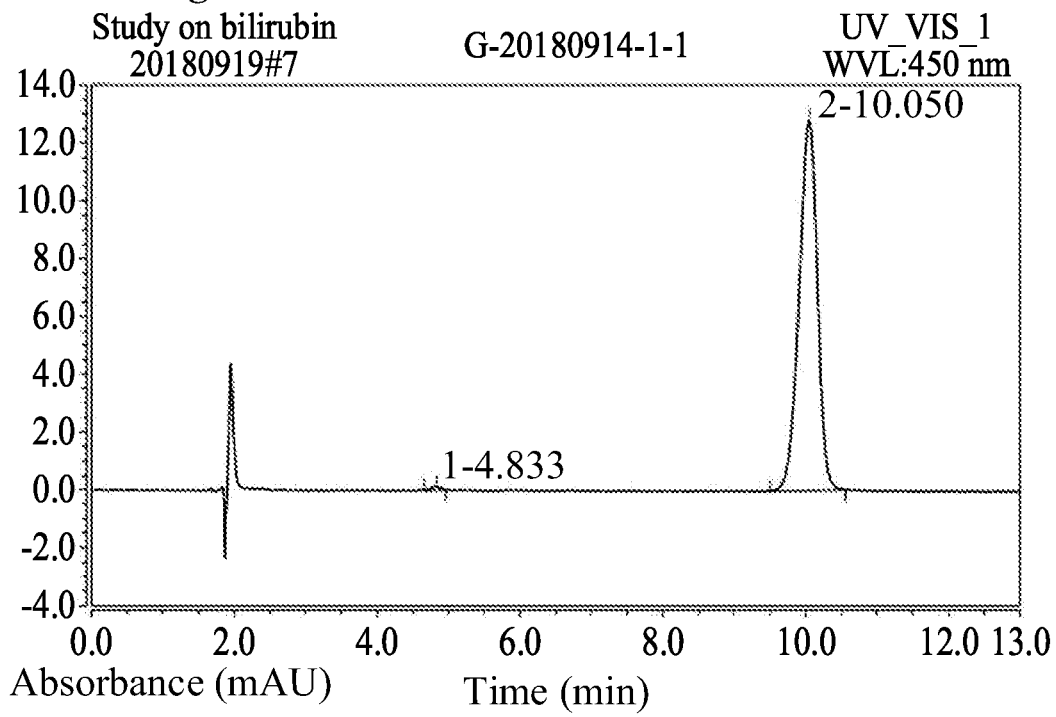
FIG. 6 is a HPLC spectrogram of bilirubin IXα in Example 2.

The purity of bilirubin IXα was 97.1%. The HPLC chromatogram was shown in FIG. 6.

B) Using Sodium Borohydride as Reducing Agent
The operations were basically the same as that in A) except that zinc borohydride was replaced by 0.500 g of solid sodium borohydride (13.2 mmol), and the resulting product contained obvious origin (polarity) impurities under TLC. The product was purified by 50 mL of 1:1 (v/v) methanol-chloroform, and 0.207 g of orange-red powders were obtained. TLC showed that there was no impurity, and the yield was 68.7%.

C) Using Potassium Borohydride as Reducing Agent
The operations were basically the same as that in A) except that zinc borohydride was replaced by 0.500 g of solid potassium borohydride (9.27 mmol), and the resulting product contained obvious origin (polarity) impurities under TLC. The product was purified by 50 mL of 1:1 (v/v) methanol-chloroform, and 0.918 g of orange-red powders were obtained. TLC showed that there was no impurity, and the yield was 65.8%.

D) Using Lithium Borohydride as Reducing Agent

The operations were basically the same as that in A) except that zinc borohydride was replaced by 1.00 g of solid potassium borohydride (45.9 mmol), and the resulting product contained obvious origin (polarity) impurities under TLC. The product was purified by 50 mL of 1:1 (v/v) methanol-chloroform, and 0.181 g of orange-red powders were obtained. TLC showed that there was no impurity, and the yield was 60.1%.

It will be obvious to those skilled in the art that changes and modifications may be made, and therefore, the aim in the appended claims is to cover all such changes and modifications.

What is claimed is:

1. A method of preparing bilirubin IXα, the method comprising:
   a) adding sodium hydroxide dissolved in a first methanol solution to biliverdin IXα diester dissolved in a second methanol solution at 5-30° C., to yield a first mixture; adding water to the first mixture to hydrolyze biliverdin IXα diester at 5-30° C.; adding an acid to the first mixture to adjust a pH value thereof to between 4 and 5; removing a first solvent of the first mixture through rotary evaporation, and removing an inorganic salt through rinsing, and vacuum drying, to yield biliverdin IXα; and
   b) dissolving the biliverdin IXα in an alcoholic solution, and adding a radical scavenger and borohydride to the alcoholic solution, to yield a second mixture where the biliverdin IXα is reduced; adding a ketone to the second mixture to decompose excess borohydride; adding the acid to the second mixture to adjust a pH value thereof to between 4 and 5; removing a second solvent of the second mixture through rotary evaporation, and rinsing, and refining with methanol-chloroform to yield bilirubin IXα having a purity of 97%.

2. The method of claim 1, wherein in a), the biliverdin IXα diester is hydrolyzed at 10-15° C.

3. The method of claim 1, wherein in b), the radical scavenger comprises an alkylphenol.

4. The method of claim 3, wherein the alkylphenol is tert butyl hydroquinone.

5. The method of claim 1, wherein in b), the radical scavenger accounts for is 0.05-0.5 wt. % of the biliverdin IXα.

6. The method of claim 5, wherein the radical scavenger is 0.1-0.2 wt. % of the biliverdin IXα.

7. The method of claim 1, wherein in b), the borohydride is selected from the group consisting of zinc borohydride, lithium borohydride, sodium borohydride, and potassium borohydride.

8. The method of claim 7, wherein the borohydride is zinc borohydride.

9. The method of claim 1, wherein in b), the ketone comprises acetone.

10. The method of claim 1, wherein in b), the reduction of the biliverdin IXα is monitored by thin layer chromatography (TLC); when the biliverdin IXα is reduced completely, the ketone is added to the second mixture to decompose excess borohydride.

11. The method of claim 1, wherein the acid comprises acetic acid.

12. The method of claim 11, wherein a concentration of acetic acid is 10%.

* * * * *